(12) United States Patent
Li

(10) Patent No.: US 8,690,825 B2
(45) Date of Patent: Apr. 8, 2014

(54) SAFETY SYRINGE

(75) Inventor: Zhi Yun Li, Jiangsu Province (CN)

(73) Assignee: Sunwell Biotech Co., Ltd., Nantong (CN)

( * ) Notice: Subject to any disclaimer, the term of this patent is extended or adjusted under 35 U.S.C. 154(b) by 84 days.

(21) Appl. No.: 12/988,134

(22) PCT Filed: Apr. 15, 2009

(86) PCT No.: PCT/CN2009/000397
§ 371 (c)(1),
(2), (4) Date: Jun. 29, 2011

(87) PCT Pub. No.: WO2009/127122
PCT Pub. Date: Oct. 22, 2009

(65) Prior Publication Data
US 2011/0264040 A1    Oct. 27, 2011

(30) Foreign Application Priority Data
Apr. 16, 2008  (CN) .................. 2008 2 0105111 U

(51) Int. Cl.
*A61M 5/00* (2006.01)
*A61M 5/32* (2006.01)

(52) U.S. Cl.
USPC .......................................... 604/110; 604/195

(58) Field of Classification Search
USPC ......... 604/110, 181, 187, 195, 218–231, 192, 604/194, 196, 240, 242, 243
See application file for complete search history.

(56) References Cited

U.S. PATENT DOCUMENTS

| 4,994,034 A | * | 2/1991 | Botich et al. .................. 604/110 |
| 5,833,660 A |   | 11/1998 | Nathan et al. |
| 2007/0260180 A1 | * | 11/2007 | Smith et al. .................. 604/110 |

FOREIGN PATENT DOCUMENTS

| CN | 2344032 Y | 10/1999 |
| CN | 1325736 A | 12/2001 |
| CN | 1406643 A | 4/2003 |
| CN | 1743018 A | 3/2006 |
| CN | 1751754 A | 3/2006 |
| CN | 2838643 Y | 11/2006 |
| CN | 101104087 A | 1/2008 |
| CN | 201194970 Y | 2/2009 |
| WO | WO-95/03845 | 2/1995 |

* cited by examiner

*Primary Examiner* — Nicholas Lucchesi
*Assistant Examiner* — Niyati D Shah
(74) *Attorney, Agent, or Firm* — Rosenberg, Klein & Lee

(57) ABSTRACT

The present invention relates to a safety syringe. The safety syringe comprises a barrel having a plurality of elastic support units in the inner side, a plunger having a rubber ring and a first coupling portion at the front-end, and an injection head unit comprising a first needle seat, a second needle seat, and a needle, wherein the second needle seat comprises a second coupling portion. When the injection head unit is mounted on the front-end opening, the second needle seat is propped by the plurality of elastic support units preventing the needle seat from being crushed during injection. After injecting, the first coupling portion is pushed to couple with the second coupling portion, and then the needle can be pulled into the barrel for safety.

7 Claims, 7 Drawing Sheets

SAFETY SYRINGE

FIELD OF THE INVENTION

The present invention relates to a safety syringe, and more particularly to a safety syringe that prevents the needle seat from being crushed while injecting and from being reused after injection.

BACKGROUND OF THE INVENTION

In medicine, a syringe is usually used for blood sample collection or drug injections.

Referring to FIG. 1, a conventional syringe 10 comprises a barrel 11, a plunger 12, a needle seat 131, a needle 133, and a tip protector 14. A rubber ring 121 is disposed at one end of the plunger 12. The plunger 12 can be placed into the barrel 11 from the second opening 112 of the barrel 11. The needle 133 is fixed in one end of the needle seat 131. The other end of the needle seat 131 is connected to the first opening 111 of the barrel 11. By pulling or pushing the plunger 12, a liquid can be drawn into the barrel 11 or pushed out of the barrel 11. The collection of blood samples and injection of drugs can be achieved by using the syringe 10. After using the syringe 10, the needle 133 and the needle seat 131 are sheathed in the tip protector 14 for safety.

SUMMARY OF THE INVENTION

It is an objective of the present invention to provide a safety syringe, and more particularly a safety syringe that prevents the needle seat from being crushed while injecting and from being reused after injection.

It is another objective of the present invention to provide a safety syringe comprising a plurality of elastic support units for supporting the second needle seat to prevent the needle seat from being crushed while injecting.

It is another objective of the present invention to provide a safety syringe comprising a first coupling portion on the plunger and a second coupling portion in the second needle seat. By coupling the first coupling portion with the second coupling portion, the plunger can pull the needle into the barrel.

It is another objective of the present invention to provide a safety syringe comprising a jostling portion on the plunger for jostling the elastic support unit out of the second needle seat. Then, the plunger can pull the second needle seat and the needle into the barrel.

It is another objective of the present invention to provide a safety syringe comprising a first thread on the first needle seat and a second thread in the front-end opening of the barrel, so that the first needle seat can be screwed onto the barrel tightly.

It is another objective of the present invention to provide a safety syringe, wherein the plunger wedges in the barrel when the needle is retracted into the barrel.

It is another objective of the present invention to provide a safety syringe, wherein the first coupling portion is hollow for easily coupling with the second coupling portion.

It is another objective of the present invention to provide a safety syringe, wherein the plunger comprises a conical section for breaking the plunger after the needle is retracted into the barrel.

The present invention provides a safety syringe, comprising: a barrel having a front-end opening, a rear-end opening, and a plurality of elastic support units disposed in the inner side of the front-end opening; a plunger having a jostling portion at the front-end, a first coupling portion disposed at the top of the jostling portion, and a rubber ring mounted around the lower portion of the jostling portion; wherein the front-end of the plunger can be put into the barrel from the rear-end opening of the barrel; and an injection head unit comprising a first needle seat, a second needle seat and a needle; wherein the first needle seat has an inner tube for holding the second needle seat, and the needle is mounted in the front-end of the second needle seat, and a second coupling portion is disposed in the rear-end of the second needle seat; when the first needle seat is mounted on the front-end opening of the barrel, the rear-end of the second needle seat is propped by the plurality of elastic support units; and when the first coupling portion is pushed to couple with the second coupling portion, the plurality of elastic support units are jostled out of the second needle seat by the jostling portion, which allows the second needle seat and the needle to be pulled into the barrel by the plunger.

The present invention further provides a safety syringe, comprising: a barrel having a front-end opening and a rear-end opening; a plunger having a first coupling portion at the front-end and a rubber ring mounted around the rear portion of the first coupling portion; wherein the front-end of the plunger can be put into the barrel from the rear-end opening of the barrel; and an injection head unit comprising a first needle seat, a second needle seat, and a needle; wherein the first needle seat has an inner tube for holding the second needle seat, and the needle is mounted in the front-end of the second needle seat, and a second coupling portion with a bump is disposed in the rear-end of the second needle seat; wherein the first needle seat can be mounted on the front-end opening of the barrel, and the first coupling portion can be pushed to couple with the second coupling portion; and when the second needle seat and the needle are pulled into the barrel by the plunger, the needle inclines because of the stress between the first coupling portion and the bump.

DETAILED DESCRIPTION OF DISCLOSED EMBODIMENTS

Figure 1:
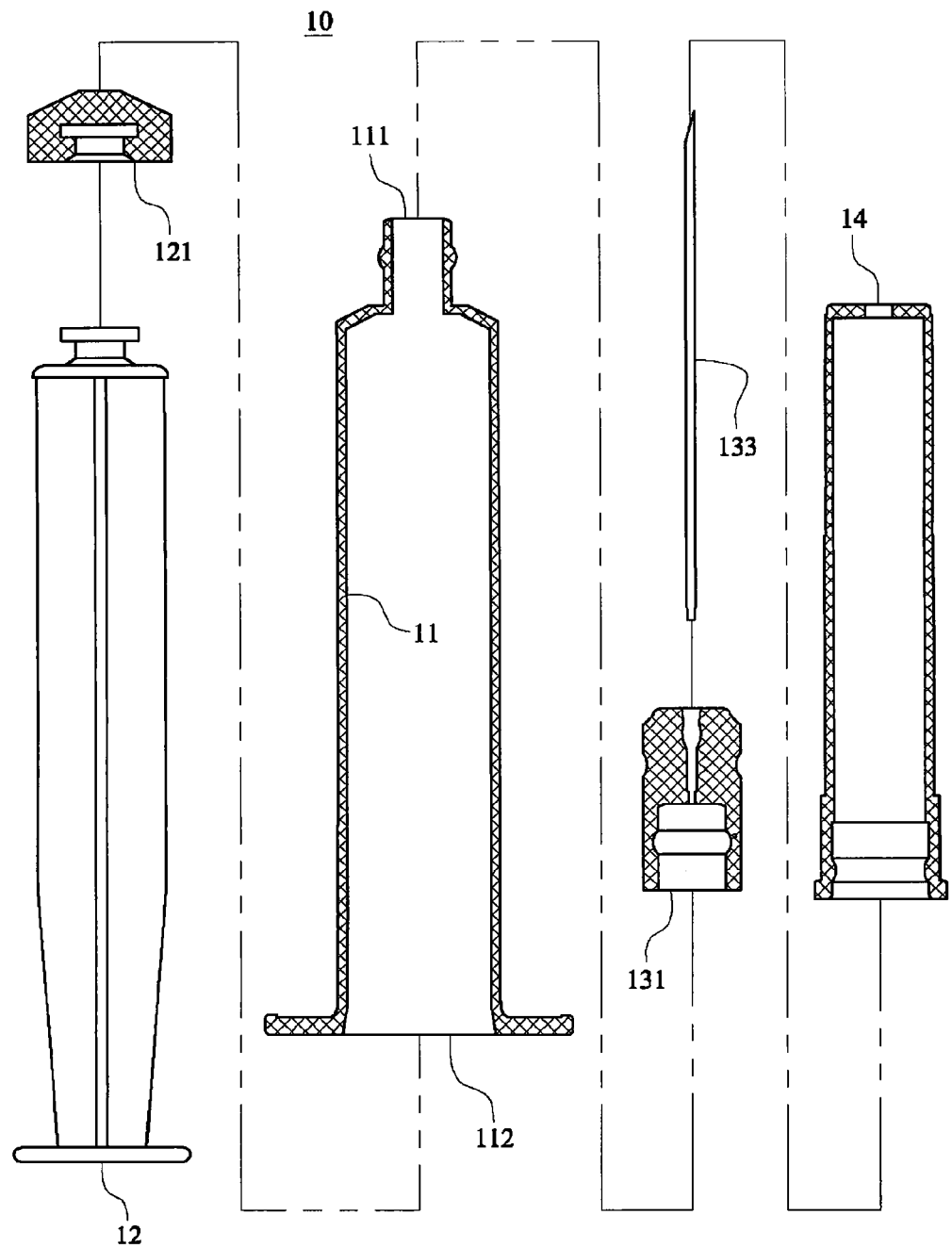
FIG. 1 is an exploded structure diagram of a traditional safety syringe.
Figure 2:
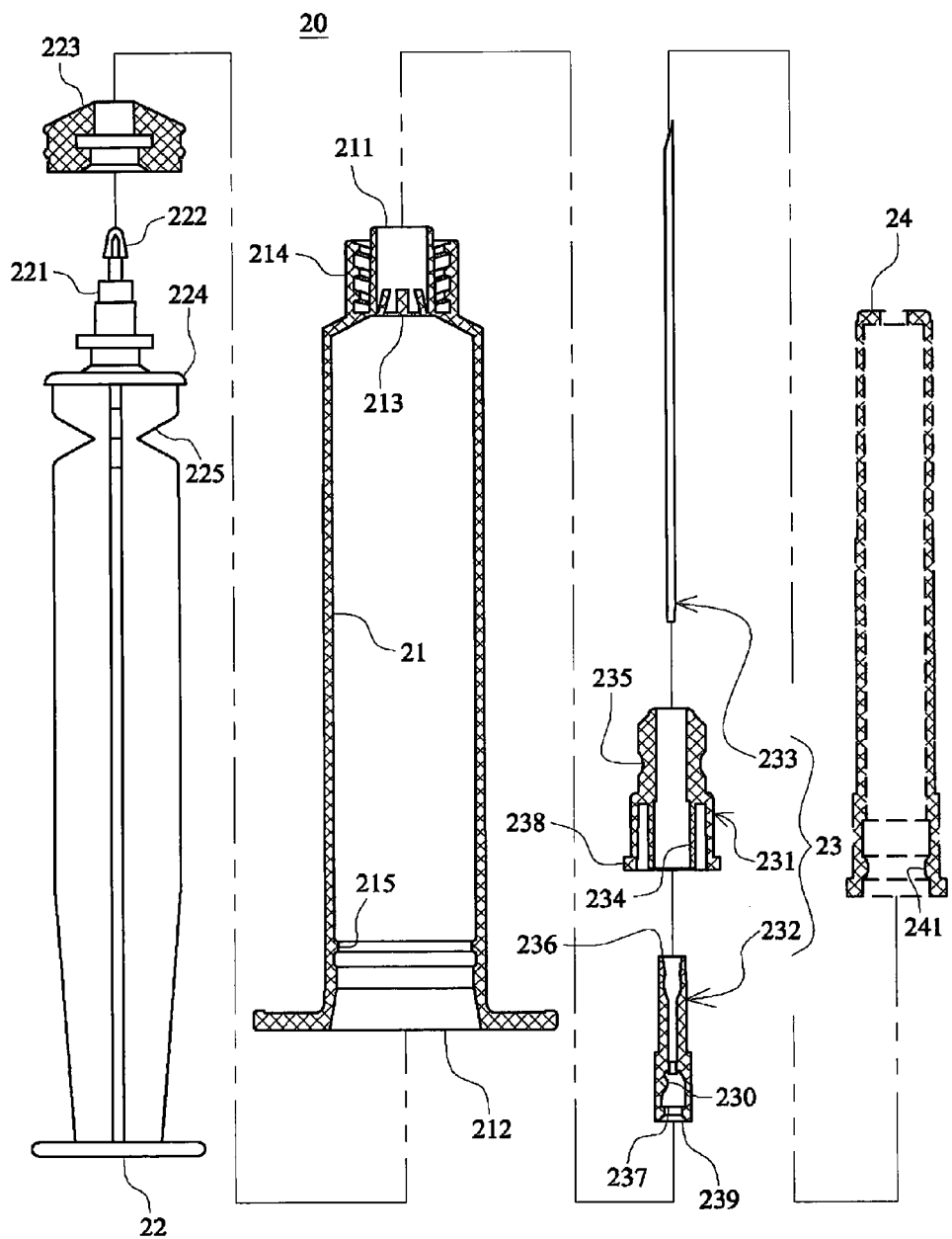
FIG. 2 is an exploded structure diagram of a safety syringe in accordance with one embodiment of the present invention.
Figure 3:
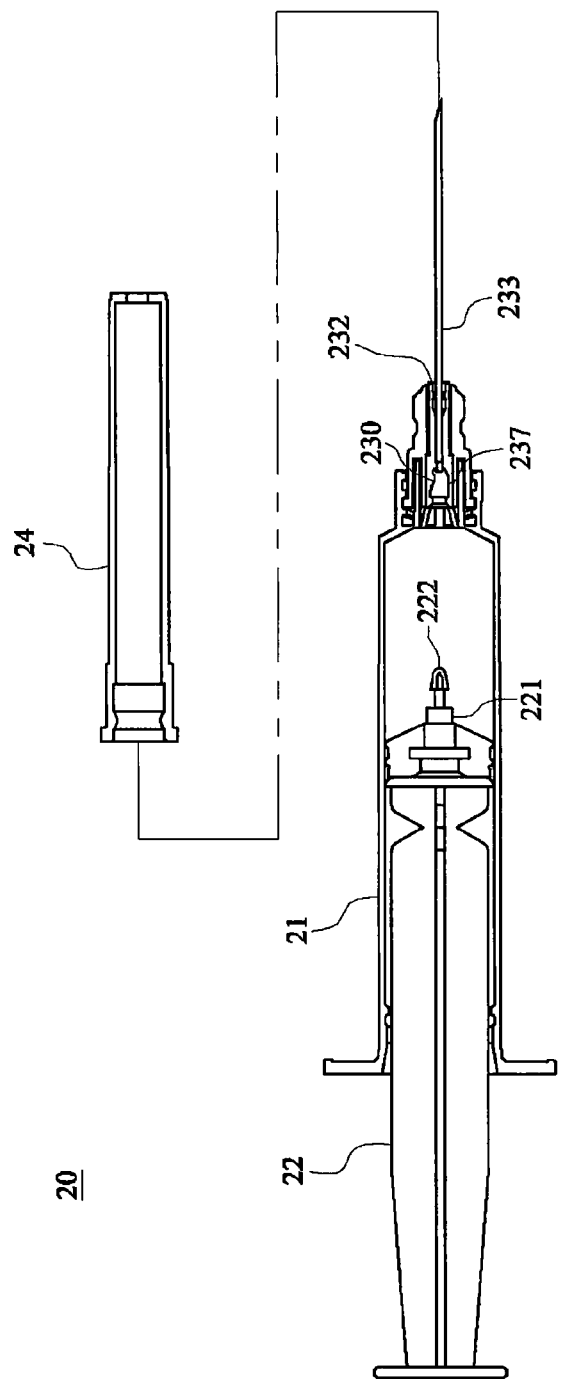
FIG. 3 is an assembly diagram of a safety syringe in accordance with the embodiment shown in FIG. 2.

Referring to FIG. 2 and FIG. 3, there are shown an exploded structure diagram and an assembly diagram of a safety syringe in accordance with one embodiment of the present invention. The safety syringe 20 comprises a barrel 21, a plunger 22, and an injection head unit 283. The barrel 21 is hollow and has a front-end opening 211 and a rear-end opening 212. A plurality of elastic support units 213 is disposed in the inner side of the front-end opening 211. The plunger 22 comprises a jostling portion 221 disposed to the front-end. A first coupling portion 222 is disposed at the top of the jostling portion 221. A rubber ring 223 is mounted around the lower portion of the jostling portion 221. The front-end of the plunger 22 with the rubber ring 223 can be put into the barrel 21 from the rear-end opening 212 of the barrel 21. The injection head unit 283 comprises a first needle seat 231, a second needle seat 232, and a needle 233. The first needle seat 231 has an inner tube 234 for holding the second needle seat 232. The second needle seat 232 has a front-end 236 and a rear-end 239. The needle 233 is mounted in the front-end 236 of the second needle seat 232. A second coupling portion 237 is disposed in the rear-end 239 of the second needle seat 232. When the first needle seat 231 is mounted on the front-end opening 211 of the barrel 21, the rear-end 239 of the second needle seat 232 is propped by the plurality of elastic support units 213. When the first coupling portion 222 is pushed to couple with the second coupling portion 237, the plurality of elastic support units 213 is jostled out of the second needle seat 232 by the jostling portion 221, and then the second needle seat 232 and the needle 233 can be pulled into the barrel 21 by the plunger 22.

Before the jostling portion 221 jostles the plurality of elastic support units 213, the rear-end 239 of the second needle seat 232 is propped by the plurality of elastic supporting units 213. This prevents the second needle seat 232 from being crushed when injecting, and drug injection can easily be completed.

After injecting, the first coupling portion 222 is pushed to couple with the second coupling portion 237 by the plunger 22, and the plurality of elastic supporting units 213 is jostled out of the second needle seat 232 by the jostling portion 221. Then, by pulling the plunger 22, the second needle seat 232 and the needle 233 are retracted into the barrel 21 preventing the safety syringe 20 from being reused.

In one embodiment of the present invention, the first needle seat 231 has a first thread 238 at the outer surface; the barrel 21 comprises a second thread 214 disposed at the inner surface of the outer tube (not numbered) of the front-end opening 211; wherein the first thread 238 mates with the second thread 214. When the first needle seat 231 is screwed into the right position on the barrel 21, the rear-end 239 of the second needle seat 232 will be propped by the plurality of elastic supporting units 213. This prevents the second needle seat 232 from being crushed while the needle 233 pierces a body.

Since the first needle seat 231 is screwed on the barrel 21, it will not become loose during transportation. And, it is easy for people to choose a suitable injection head unit 23 by screwing the first needle seat 231 onto or off of the barrel 21.

The safety syringe 20 in accordance with the present invention further comprises a tip protector 24 for protecting the needle 233. The tip protector 24 has a flange 241 at the inner side. The first needle seat 231 has a groove 235 that mates with the flange 241 of the tip protector 24, such that the tip protector 24 can be fixed on the first needle seat 231.

Of course, the tip protector 24 can be designed to couple with the first needle seat 231 by thread screwing.

The barrel 21 has a flange 215 at the inner side of the rear-end opening 212. The plunger 22 has a flange 224 at the front-end. When the plunger 22 is pulled back with the needle 233 and the second needle seat 232, the flange 215 of the barrel 21 will stop the plunger 22 and prevent the plunger 22, the second needle seat 232, and the needle 233 from being pulled out of the barrel 22.

Figure 4:
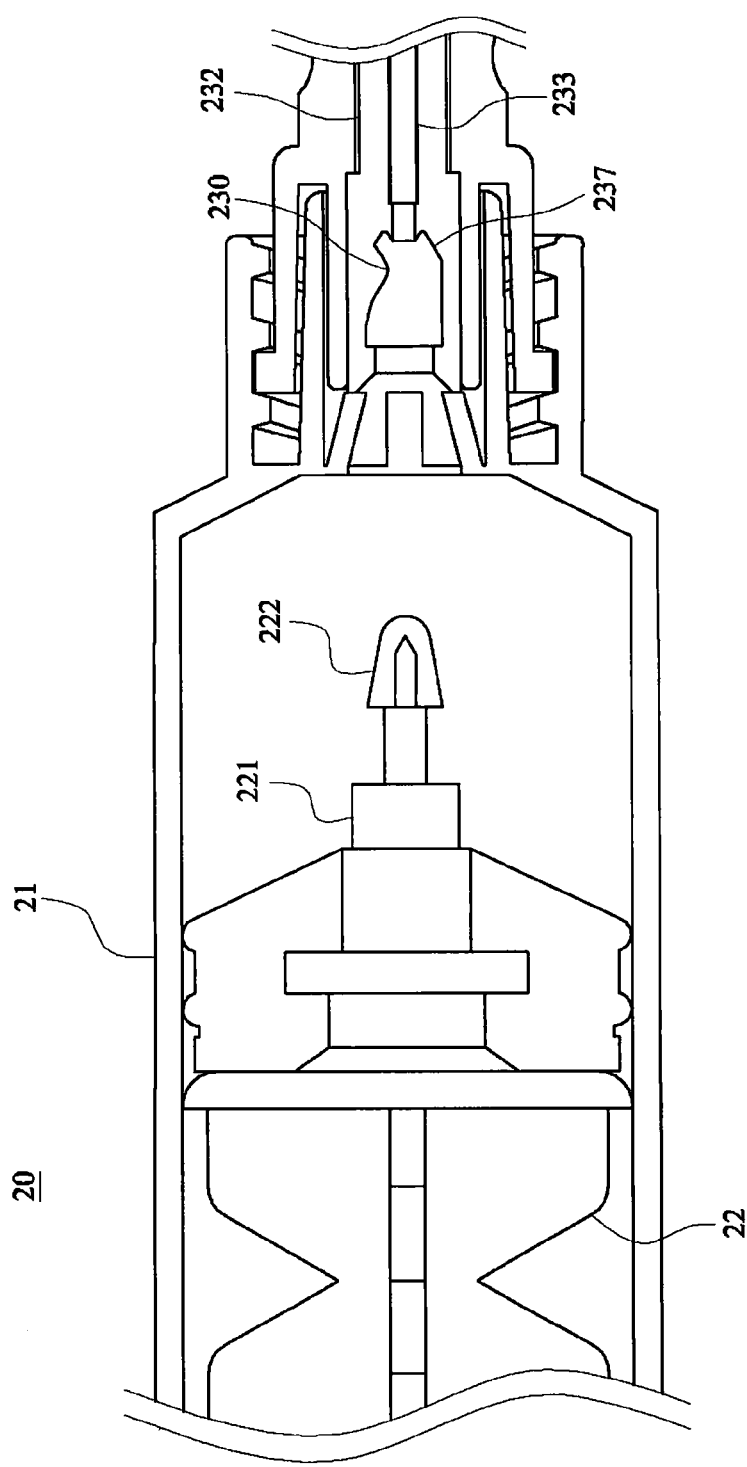
FIG. 4 is an enlarged partial structure diagram of a safety syringe in accordance with one embodiment of the present invention.
Figure 5:
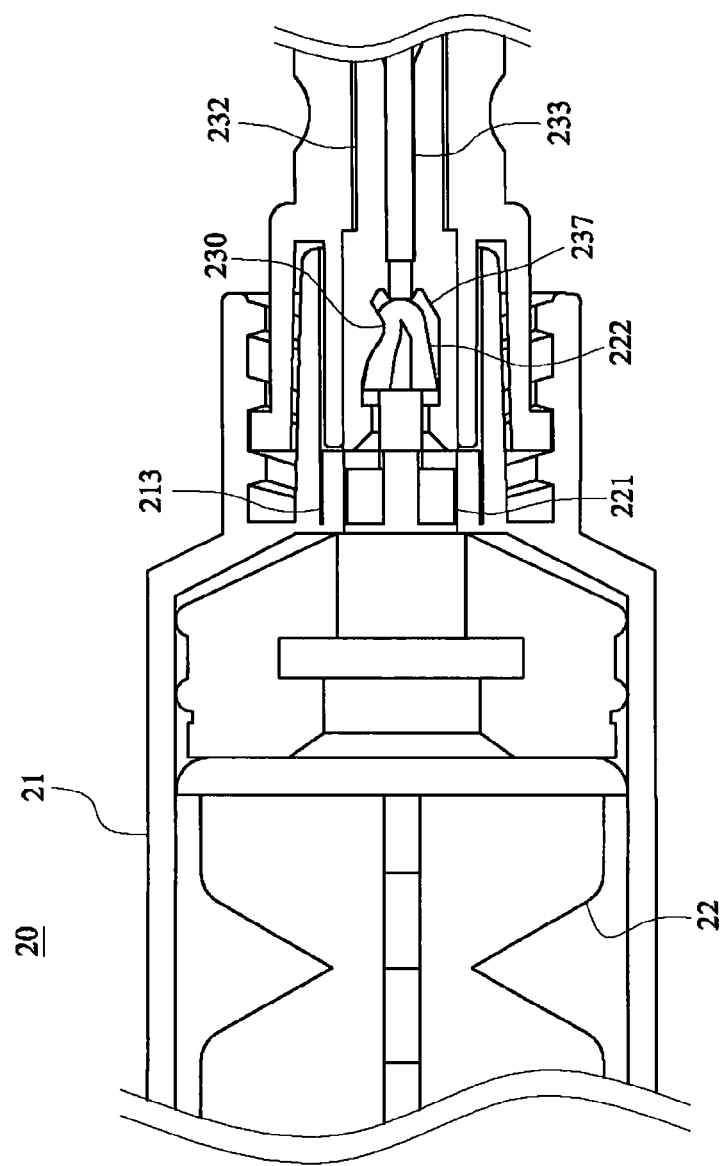
FIG. 5 is an enlarged partial structure diagram of a safety syringe in accordance with one embodiment of the present invention.
Figure 6:
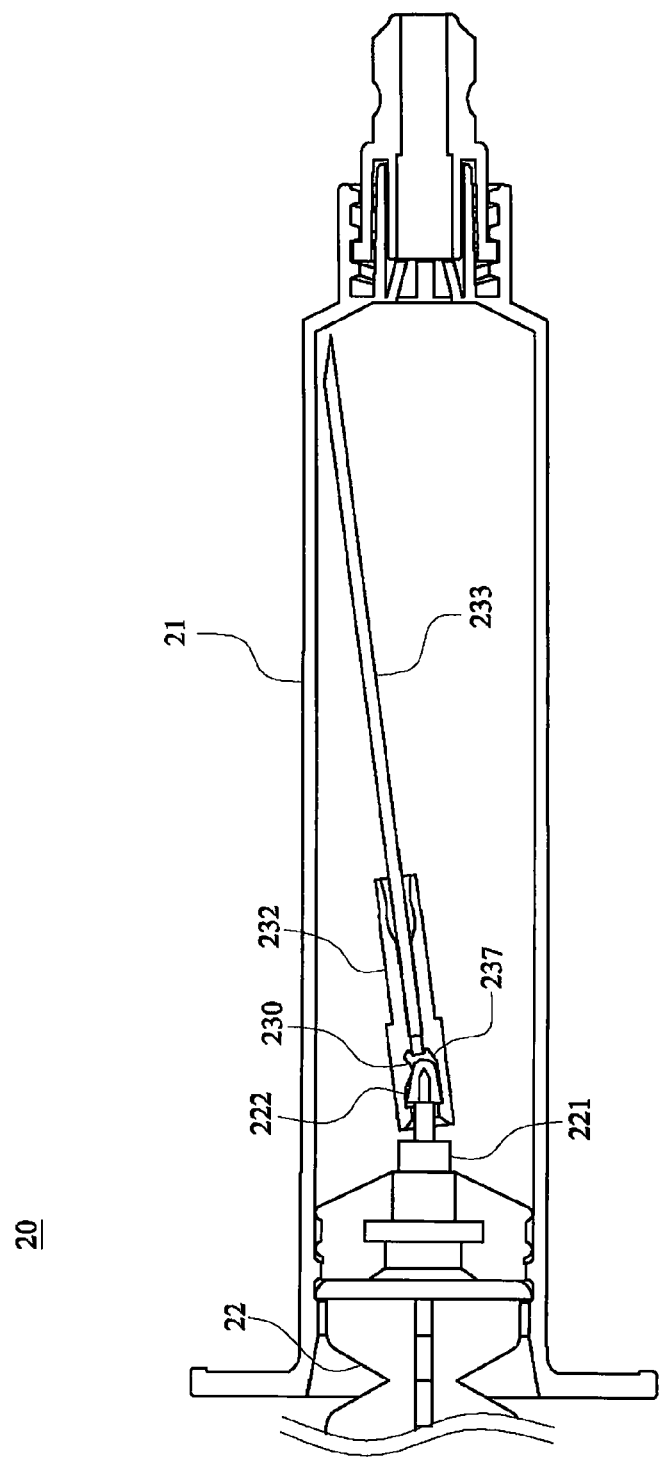
FIG. 6 is an enlarged partial structure diagram of a safety syringe in accordance with one embodiment of the present invention.

Referring to FIG. 4, there is shown an enlarged partial structure diagram of a safety syringe in accordance with one embodiment of the present invention. In the present embodiment, the first coupling portion 222 is a cone-like body, and the second coupling portion 237 is a cone-like cavity for coupling with the first coupling portion. In one embodiment of the present invention, the second coupling portion 237 further comprises a bump 230 in the cavity. When the second needle seat 232 and the needle 233 are pulled into the barrel 21, the needle 233 inclines towards the direction of the bump 230 because of the stress between the first coupling portion 222 and the bump 230. This prevents the needle 233 from being exposed through the front-end opening 211. In one embodiment of the present invention, the first coupling portion 222 is hollow and more elastic that is advantageous for coupling with the second coupling portion 237.

Referring to FIG. 3, FIG. 4, FIG. 5, and FIG. 6, there are shown an assembly diagram, and enlarged partial structure diagrams of a safety syringe in accordance with one embodiment of the present invention. After the safety syringe 20 is assembled, the safety syringe 20 can draw a liquid into the barrel 21 by pulling the plunger 22. When injecting, the safety syringe 20 squeezes the liquid out of the barrel 21 by pushing the plunger 22. After injecting, the plurality of elastic supporting units 213 is jostled out of the second needle seat 232 by the jostling portion 221, and the first coupling portion 222 is pushed into the cavity of the second coupling portion 237 and couples with the second coupling portion 237. By pulling the plunger 22, the second needle seat 232 and the needle 233 are retracted into the barrel 21; then, the needle 233 inclines towards the direction of the bump 230 because of the stress between the first coupling portion 222 and the bump 230. This prevents the needle 233 from being exposed through the front-end opening 211.

Figure 7:
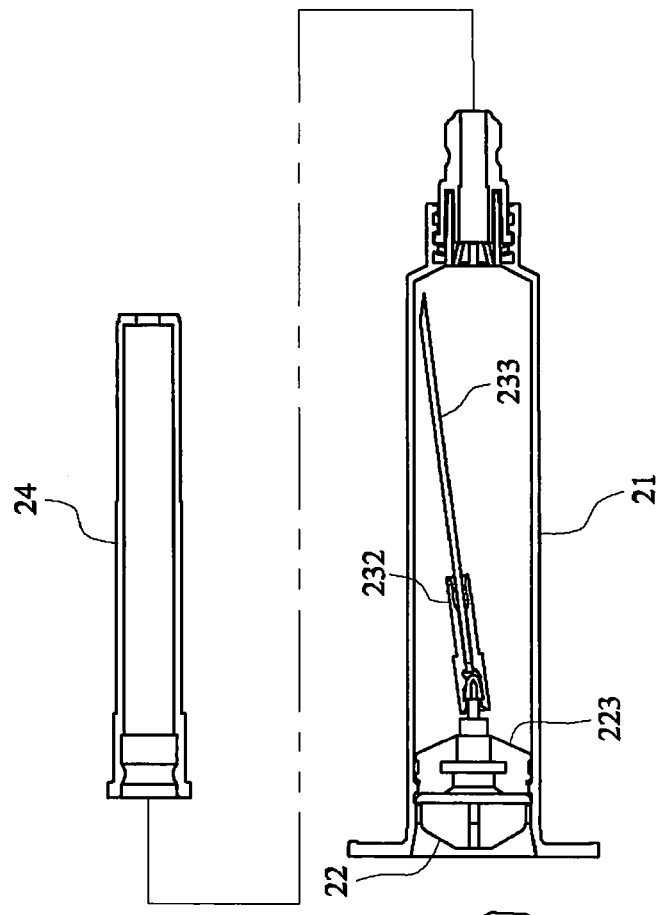
FIG. 7 is a schematic diagram showing the plunger of the safety syringe in accordance with one embodiment of the present invention, wherein the plunger pulls the needle into the barrel and is broken.

Referring to FIG. 7, there is shown a schematic diagram of a safety syringe in accordance with one embodiment of the present invention. In the present embodiment, the plunger 22 has a conical section 225 (as shown in FIG. 2). After pulling the second needle seat 232 and the needle 233 into the barrel 21, the plunger 22 can be broken at the conical section 225. The front-end of the plunger 22 is left in the barrel 21, and is difficult to be removed from the barrel 21 because of the flanges 215 and 224 of the barrel 21 and the plunger 22.

The present invention is not limited to the above-described embodiments. Various alternatives, modifications, and equivalents may be used. Therefore, the above embodiments should not be taken as limiting the scope of the invention, which is defined by the appending claims.

What is claimed is:

1. A safety syringe, comprising:
    a barrel having a front-end opening, a rear-end opening and a plurality of elastic support units disposed in an inner side of the front-end opening;
    a plunger having a jostling portion at a front-end thereof, a first coupling portion disposed at a top of the jostling portion, and a rubber ring mounted around a lower portion of the jostling portion; wherein the front-end of the plunger is inserted into the barrel from the rear-end opening of the barrel; and
    an injection head unit comprising a first needle seat, a second needle seat, and a needle;
    wherein the first needle seat has an inner tube for holding the second needle seat, and the needle is mounted in a front-end of the second needle seat, and a second coupling portion is disposed in a rear-end of the second needle seat; when the first needle seat is mounted on the front-end opening of the barrel, the rear-end of the second needle seat is propped by the plurality of elastic support units; and when the first coupling portion is pushed to couple with the second coupling portion, the plurality of elastic support units is jostled out of the second needle seat by the jostling portion, and then the second needle seat and the needle are pulled into the barrel responsive to pulling the plunger;

wherein the first coupling portion is a cone-like body, and the second coupling portion is a cone-like cavity having a bump protruding into the cone-like cavity; engagement between the cone-like body and the cone-like cavity forces contact between an inclined side of the cone-like body and the protruding bump to apply a stress to a side of the second needle seat so that when the second needle seat and the needle are pulled into the barrel, the needle is forced to incline as a result of the stress applied to the second needle seat.

2. The safety syringe of claim 1, wherein the first needle seat has a first thread at an outer surface and the barrel comprises a second thread disposed at an inner surface of an outer tube of the front-end opening; wherein the first thread mates with the second thread.

3. The safety syringe of claim 1, further comprising a tip protector having a flange at an inner side thereof, and the first needle seat having a groove for mating with the flange of the tip protector.

4. The safety syringe of claim 1, wherein the barrel comprises a flange at an inner side of the rear-end opening, and the plunger has a flange at the front-end.

5. The safety syringe of claim 1, wherein the plunger has a conical section.

6. The safety syringe of claim 1, wherein the first coupling portion has a closed hollow structure.

7. The safety syringe of claim 6, wherein the first coupling portion is elastic.

* * * * *